United States Patent [19]

Becker

[11] 4,273,622
[45] Jun. 16, 1981

[54] METHOD OF TREATING ALPHA-METHYLBENZYLALCOHOL DEHYDRATION PRODUCTS

[75] Inventor: Mitchell Becker, Teaneck, N.J.

[73] Assignee: Halcon Research & Development Corp., New York, N.Y.

[21] Appl. No.: 97,452

[22] Filed: Nov. 26, 1979

Related U.S. Application Data

[63] Continuation of Ser. No. 918,124, Jun. 22, 1978, abandoned, which is a continuation-in-part of Ser. No. 870,543, Jan. 16, 1978, abandoned.

[51] Int. Cl.³ .......................... B01D 3/10; C07C 7/04; C07C 15/46
[52] U.S. Cl. ........................................ 203/28; 203/71; 203/80; 585/437; 585/800; 585/806
[58] Field of Search ..................... 203/80, 73, 71, 91, 203/6, 8, 9, 28; 585/437, 805, 806, 800

[56] References Cited

U.S. PATENT DOCUMENTS

| | | | |
|---|---|---|---|
| 1,640,975 | 8/1927 | Brown | 203/28 |
| 2,370,948 | 3/1945 | Gadwa | 203/75 |
| 2,457,361 | 12/1948 | Gadwa | 203/80 |
| 2,614,070 | 10/1952 | Smith | 203/28 |
| 3,084,108 | 4/1963 | Randall | 203/91 |
| 3,452,055 | 6/1969 | Golden et al. | 585/437 X |
| 3,457,291 | 7/1969 | Baylor | 203/28 |
| 3,515,647 | 6/1970 | Van Tassell | 203/80 |
| 3,526,674 | 9/1970 | Becker et al. | 585/437 |
| 3,629,076 | 12/1971 | Jones | 585/2 |
| 3,658,928 | 4/1972 | Skinner et al. | 585/437 |

FOREIGN PATENT DOCUMENTS 589015  6/1947  United Kingdom .

*Primary Examiner*—Wilbur L. Bascomb, Jr.
*Attorney, Agent, or Firm*—William C. Long; David Dick; Riggs T. Stewart

[57] ABSTRACT

Residual products obtained in the catalytic dehydration of alpha-methylbenzyl alcohol are treated to recover monomeric styrene values by a process which comprises fractionally distilling the residual products in two stages under different temperature and time conditions.

10 Claims, No Drawings

METHOD OF TREATING ALPHA-METHYLBENZYLALCOHOL DEHYDRATION PRODUCTS

CROSS REFERENCE TO RELATED APPLICATION

This is a continuation, of application Ser. No. 918,124 filed June 22, 1978, now abandoned which is a continuation-in-part of co-pending application Ser. No. 870,543, filed Jan. 16, 1978 now abandoned.

This invention relates to the dehydration of alpha-methylbenzyl alcohol (also known as alpha-phenylethanol or methyl phenyl carbinol) to produce styrene and is more particularly concerned with the recovery of valuable monomeric compounds from residual materials produced in the separation of components of the dehydrated mixture.

Monomeric styrene, which is readily converted by co- and homo-polymerization into a variety of useful plastics and elastomers, has enjoyed phenomenal success as a chemical of commerce and many billions of pounds of this monomer are produced annually in the United States alone. Until recently, however, commercial production of styrene monomer has been limited almost exclusively to a process involving the catalytic-vapor-phase dehydrogenation of ethylbenzene. This route is described, for example, in Kirk-Othmer "Encyclopedia of Chemical Technology" (2nd Ed.) Vol. 19, pp. 63-68. Other routes to styrene have been proposed in the past, but they failed to be competitive with the ethylbenzene dehydrogenation technology. In accordance with one of these earlier processes by which monomeric styrene was produced commercially for a short period of time, ethylbenzene was oxidized to acetophenone in the liquid phase, then the ketone was hydrogenated to alpha-methylbenzyl alcohol, and this alcohol was catalytically dehydrated to styrene. This process is described, for example, in Kirk-Othmer, "Encyclopedia of Chemical Technology", 1954, Vol. 13, pp. 134-6.

More recently a commercially attractive process which includes the dehydration of alpha-methylbenzyl alcohol has been disclosed. This new technology, known as the Halcon process, is described on pages 62-63 of the above-mentioned Vol. 19 of the 2nd edition of the Kirk-Othmer text. The dehydration of the alpha-methylbenzyl alcohol can be effected in any convenient manner, either in the liquid phase or in the vapor phase, for example by methods such as described in U.S. Pat. No. 3,658,928. Liquid-phase methods are preferred, however, because the catalysts used in vapor-phase operations require frequent regeneration to maintain acceptable conversion and selectivity values. Regeneration of catalysts in such processes involves the removal by burning of the deposited carbonaceous materials which coat the catalyst and inhibit its activity. The removal of such deposits by burning, however, creates significant problems. For example, high temperatures are developed during the burning and, in order to withstand these temperatures, the use of alloy steel or the like is required since ordinary carbon steels do not have sufficient strength to withstand the temperatures developed. Moreover, such deposits represent an economic loss since their burning converts them entirely into waste gases with no possibility of recovering valuable compounds from them. Liquid-phase dehydration processes avoid such problems and a particularly attractive process is described in Becker et al U.S. Pat. No. 3,526,674 of Sept. 1, 1970, the disclosure of which patent is incorporated herein by reference.

In liquid-phase processes residual fractions containing complex oligomers and polymers are obtained, but these residual materials are ordinarily retained in the dehydration system, except for a relatively small purge to prevent an undesired build-up. Thus, in the process described in the abovementioned U.S. Pat. No. 3,526,674 alpha-methylbenzyl alcohol is subjected to catalytic dehydration in the presence of a liquid-phase reaction medium at a temperature above about 200° C., but below the decomposition temperature of the liquid-phase reaction medium and in the presence of an appropriate catalyst, e.g., a mineral acid, an organo-sulphonic acid, a carboxylic acid, or a high-surface-area alumina.

Ordinarily, the liquid-phase reaction medium is provided by accumulating a sufficient quantity of the residual material referred to above which is formed during the dehydration reaction, and this residual material can be the sole liquid-phase reaction medium or it can be admixed with either polar or non-polar relatively high-boiling solvents of the type described in U.S. Pat. No. 3,526,674. During the course of the reaction, the alpha-methylbenzyl alcohol forms water and the desired styrene and, under the reaction conditions employed, the water and the styrene are volatilized substantially as rapidly as they are formed and are, therefore, readily removed from the reaction zone. Alpha-methylbenzyl alcohol, which can also be volatilized as the reaction proceeds, is suitably condensed and returned to the reaction zone. High selectivities to the formation of styrene are obtained, i.e., reaction selectivities of the order of 90% or more are readily achieved. The small amounts of the high-boiling residual by-products remain essentially unvolatilized and are purged from the liquid-phase reaction medium, periodically or continuously, when they accumulate to an undesired extent.

The purge stream which is thus withdrawn from the liquid phase reaction medium ordinarily represents a very minor quantity and its withdrawal does not affect the commercial attractiveness of the process. It is apparent, however, that if this purge stream could be treated so that it could be made to yield additional quantities of styrene and styrene precursors the over-all selectivity of the process to styrene would be increased and, when calculated in terms of millions or billions of pounds, significant economic benefits would obviously accrue, and waste disposal problems would be significantly reduced. The term "styrene precursors" is used herein to designate $C_8$ compounds such as ethylbenzene (EB), methylbenzyl alcohol (MBA), acetophenone (ACP) and like compounds readily convertible to styrene. The high-boiling residual material of which the purge stream is composed is, however, as previously mentioned, highly oligomeric and ploymeric in nature and efforts to derive monomeric styrene values (styrene and styrene precursors) from such residues have, up to now, not been successful. In the case of vapor-phase operation, a residual by-product fraction may also be recovered from the vaporous effluent from the reactor and what has been said above regarding the residual purge stream from liquid-phase dehydration is also applicable to such vapor phase residual fractions.

It is, accordingly, an object of this invention to provide a process for recovering valuable styrene monomer values from the residual portion of the reaction mixture obtained in the dehydration of alpha-methylbenzyl alcohol.

In accordance with the invention, the foregoing and other objects are realized by subjecting the residual portion of the alpha-methylbenzyl alcohol (MBA) hydrate to an integrated series of distillations wherein the residual fraction is distilled in two stages under different time and temperature conditions as will be described more specifically below.

The residual fraction or purge stream which is treated by the process of this invention is a multi-component mixture comprising not only polymeric materials but also small amounts of MBA, ACP, EB, styrene monomer (SM), water and, in the case of liquid-phase operation, catalyst.

The polymeric materials are of various degrees of polymerization and include polymeric hydrocarbons, polymeric oxygenated materials, or interpolymers or condensation products containing both hydrocarbon moieties and oxygenated moieties. Moreover, it has been found that when this residual material is directly treated at temperatures necessary to achieve depolymerization, the monomeric components which it contains react with the polymeric components to form additional polymeric substances which result in a significantly more refractory polymeric mass, causing additional problems from the standpoint of handling and recovery. It has now been surprisingly discovered, however, that by distilling this material under a specific regimen the polymeric components can be converted into significant percentages of monomeric styrene as well as other valuable monomers, and undesired reactions can be avoided.

The residual fraction which is treated in accordance with the invention can, as mentioned, be produced in any MBA dehydration process, but the invention is particularly applicable to the residual product obtained in liquid-phase dehydration operations, particularly in accordance with the disclosure of the above-mentioned Becker et al U.S. Pat. No. 3,526,674.

The process of this invention is thus readily applicable to residues or residual fractions having compositions varying over a broad range. However, as an example, a typical residual fraction or purge stream of a type readily subjected to treatment in accordance with the process of this invention may have the following composition with respect to organic components:

| Component | Wt. % |
|---|---|
| ethyl benzene (EB) | 0.05 |
| styrene (SM) | 1.0 |
| acetophenone (ACP) | 2.5 |
| alpha-methylbenzyl alcohol (MBA) | 0.4 |
| balance: polymeric materials | |

It will be understood, of course, that the residual fraction referred to above is merely roughly representative of materials obtained in purge streams or residual fractions from the dehydration of MBA and that the quantities of monomeric components can vary over a wide range depending upon the particular parameters of the dehydration operations. For example, the quantity of monomeric components may be as little as 1% or less and may amount to 20% or more. In general, however, the quantity of monomeric components will usually range from about 2 to about 10%. In any case, the polymeric component is by far the predominant portion of the residual fraction or purge stream subjected to treatment. In the case of a residual stream from liquid-phase operation, there will be a small content of catalyst, e.g., alumina, but this does not affect the recovery process of this invention. The catalyst merely remains essentially unvaporized in a final non-volatilized residue. Ordinarily the catalyst will represent 1 to 10 wt. percent of the liquid-phase purge stream.

In the first stage of the process of this invention, the residual material is subjected to fractional distillation at temperatures of 180° to 275° C. for 0.5 to 5 hours, typically 1 to 2 hours. In the second stage of the process of this invention, the high boiling or less volatile portion of the residual material which remains from the first stage distillation is fractionally distilled at a higher temperature and for a longer period of time. In this second stage, reboiler temperatures of 300° to 425° C. are observed, preferably 325° to 375° C. and the material is distilled in the second stage for 10 to 40 hours, typically 18 to 21 hours.

It is a feature of this invention that the process can be carried out in a batchwise manner or it can be carried out continuously. When carrying out the process batchwise, the first-stage distillation is carried out at subatmospheric pressures, in the range of 5 to 100 mm Hg and at a reboiler temperature of 180°-260° C. Higher or lower subatmospheric pressure can, however, be employed if desired. In the second stage of batch operation, the pressure is significantly greater than the pressure in the first stage of batch operation, e.g., by at least about 400 mm Hg e.g., at least 500 mm Hg, and most suitably and conveniently the pressure in the second stage of batch operation is about atmospheric. Superatmospheric pressure can, however, be applied if desired. When the process of the invention is carried out batchwise, the first stage can be effected in a first fractional distillation column and the second stage can be carried out in a second fractional distillation column with the high boiling component from the first stage distillation being used as feed to the second stage distillation. Alternatively, both stages can be carried out in the same distillation column. The distillation is carried out under reflux conditions such that the "heavies" (polymeric materials) do not pass into the distillate. This result is achieved, as will be obvious to persons skilled in the art, by appropriate selection and/or adjustment of the reflux ratio. Typically, in the first stage of batch operation, reflux ratios between 2:1 and 20:1, preferably between 5:1 and 15:1, are employed and reflux ratios approximating 10:1 have been found to be particularly suitable. Higher reflux ratios can be used if desired. In the second stage of batch operation, it has been found desirable to begin the distillation with a low reflux ratio, e.g., 2:1 and to increase the reflux ratio as required to prevent heavies from passing into the distillate until unduly high reflux ratios become necessary, e.g., reflux ratios higher than about 50:1, although a maximum ratio of the order of 25:1 is preferred. The suppression of heavies is conveniently gauged in conventional manner by observation of overhead temperature. Thus, in the first stage of batch operation the distillation is ordinarily continued until the overhead temperature under the pressure employed tends to exceed the boiling point of ACP and the second stage of the process is carried out until the overhead temperature tends to exceed the boiling point of styrene at the pressure employed, e.g., 146° C. at atmospheric pressure, notwithstanding adjustments in reflux ratios. Extending the distillation beyond this point will produce some additional monomer values but will also result in the passage of heavies into the distillate. Furthermore, the viscosity of the material remaining in the reboiler will increase to a point that will make it very difficult to remove.

In continuous operation of the process of the invention, a single fractional distillation column is preferably employed with the residual material to be distilled being introduced into the side of the column, typically at about the midpoint between the top and bottom of the column. In any case, the point of introduction is selected so that the feed will be initially subjected to the time and temperature parameters referred to above for first stage operation and the high boiling or less volatile components are subjected to the temperature and time parameters specified above for the second stage of the process. In continuous operation, subatmospheric, atmospheric or superatmospheric pressure can be employed but typically both stages of the continuous embodiment of the process of the invention can be carried out at about atmospheric pressure. Control of temperature in the column is, of course, readily obtained by the reflux ratio under which the column is operated, as will be obvious to persons skilled in the art.

The two stages of the process are suitably carried out in any conventional fractional distillation apparatus but the process of the invention is by no means limited to any specific type of apparatus. Ordinarily, each batch fractional distillation unit should contain at least 3 theoretical plates and the continuous unit should contain at least about 6 theoretical plates, i.e., at least about 3 rectifying plates and at least 3 stripping plates. The upper limit on theoretical plates is determined only by economic considerations.

By means of the process of this invention it is possible to recover from a residual product or purge stream which has heretofore been considered essentially valueless, up to essentially a half or more of its organic content as useful, valuable products, i.e., monomeric styrene and styrene precursors.

The following examples will serve to provide a fuller understanding of the invention, but it is to be understood that these examples are given for illustrative purposes only and are not to be interpreted as being limitative of the invention. In the examples, all parts are on a weight basis, unless otherwise indicated. Examples 1-4 illustrate batch operation, Examples A to D are comparative examples which serve to point out the significance of the two-stage process of the invention, whereas Example 8 illustrates continuous operation.

EXAMPLE 1

A reactor, constructed from a 1-liter round-bottom flask and a 15-tray 1" Oldershaw column with provision for reflux and vacuum, was charged with 700 gm of residual material produced in the dehydration of MBA and containing 8% of monomeric components. The reactor was heated under a pressure of 50 mm Hg to distill the charge. The distillation was continued until the overhead temperature exceeded the boiling point of ACP under the prevailing subatmospheric pressure (120° C.) and the reflux ratio of about 10:1. This required about one hour and the temperature in the flask was about 190° to 255° C. The residue was then further distilled under atmospheric pressure and the reflux ratio of the system was increased from about 2:1 to about 50:1 to force polymeric materials back into the flask to crack further. The distillation was continued for 20 hours until no significant distillate was produced and the distillate temperature rose above 140°-145° C. The temperature in the flask was about 315° to 360° C. In this manner 54% of the charge was recovered in the distillate and the distillate contained 40% of the charge as styrene and styrene precursors.

EXAMPLE 2

Example 1 was repeated except that the residual material charged to the reactor contained 2% of monomeric components, the vacuum distillation was continued for two hours with a temperature in the flask of about 260° C. and the atmospheric distillation was continued for twenty hours with a temperature in the flask of about 310° to about 325° C. In this case 65% of the charge was recovered in the distillate and the distillate contained 40% of the charge as styrene and styrene precursors.

EXAMPLE 3

In the preceding examples the residue charged consisted only of organic components and was free of inorganic catalyst. Catalyst such as alumina is removed when desired by filtration or other suitable means. In this example the charge of residual material corresponded to that used in Example 1 (6% monomeric components) but it also contained 5% of alumina catalyst and the example demonstrates that the presence of the catalyst has no adverse effect on the treatment of the residual material. The vacuum and atmospheric distillations were carried out as described in Example 1 except that the atmospheric distillation continued for twenty-five hours. The temperature in the flask was about 190° to 240° C. during the vacuum distillation and about 310° to 360° C. during the atmospheric distillation. In this experiment 65% of the charge was recovered as distillate and the distillate contained 45% of the charge as styrene and styrene precursors.

The following comparative examples demonstrate that vacuum treatment alone, even if prolonged, and atmospheric treatment alone for comparable periods of time result in the recovery of a significantly smaller portion of the residual material as styrene or styrene precursors even when the material charged already contains a relative high portion of monomeric materials.

COMPARATIVE EXAMPLE A

The apparatus described in Example 1 was charged with a residual material produced in the dehydration of MBA and containing 14% of monomeric components. The reactor was heated under a pressure of 50 mm Hg, and the reflux ratio of the system was maintained at about 10:1 to force polymeric materials back into the flask. The distillation was continued until the distillate temperature exceeded the boiling point of ACP under the prevailing subatmospheric pressure (120° C.), which required 12 hours. The reaction ceased at this point because the flask or reboiler temperature was too low to promote the cracking of the polymeric portion of the residue any further. The reboiler temperature during the distillation was 250° to 300° C. In this experiment 13% of the charge was obtained as distillate and the distillate contained only 12% of the charge as styrene and styrene precursors.

COMPARATIVE EXAMPLE B

Example 1 was repeated except that the vacuum distillation was omitted and the charge (6% monomeric components) was distilled under atmospheric pressure for 20 hours with the reflux ratio being increased from about 2:1 to about 50:1 as required to hold back polymeric materials. The flask or reboiler temperature was 280° to 320° C. In this manner 29% of the charge was recovered as distillate and the distillate contained only 19% of the charge as styrene and styrene precursors.

COMPARATIVE EXAMPLE C

Example 2 was repeated except that, as in Example B, the vacuum distillation was omitted and the residual material (2% monomeric components) was distilled under atmospheric pressure for 18 hours, the temperature in the flask being 310° to 350° C. In this experiment 43% of the charge was recovered as distillate and the distillate contained only 25% of the charge as styrene and styrene precursors.

COMPARATIVE EXAMPLE D

Example B was repeated except that the charge employed contained 16% monomeric components. After atmospheric distillation for 20 hours, 22% of the charge was recovered as distillate and the distillate contained only 13% of the charge in the form of styrene and styrene precursors.

EXAMPLE 4

This example illustrates continuous operation. A reactor, constructed from a 1-liter round bottomed flask and a 30-tray 1" Oldershaw fractional distillation column with provision for reflux and a feed section below the 15th tray from the top, was continuously fed with a residual material produced in the dehydration of MBA containing 8% monomeric components at the rate of 60 grams per hour. The column was operated under atmospheric pressure and the reflux ratio was held to 30:1. The temperature at the 10th tray below the feed was 230° C. and the temperature of the overhead was 140° C. The higher boiling components of the feed continuously passed into the distilling flask or reboiler which was at a temperature of 350° C. These high boiling or residual components had a residence time of about 20 hours in the distilling flask and were continuously withdrawn from the flask at a rate of 28 grams per hour. The residence time of this material on the trays of the column was about 45 minutes. The distillate rate was 32 grams per hour and the distillate contained 40% of the charge as styrene and styrene precursors. In this continuous distillation, the conditions to which the feed was subjected in the column represent the first stage of the 2-step process of this invention and the conditions to which the heavier portions of the feed which pass into the distilling flask were subjected in the flask represent the second stage of the process.

It will thus be seen that, whether carried out batchwise or continuously, the process of this invention makes it possible to recover a large portion of the organic content of a heretofore discarded residual product as useful, valuable products.

What is claimed is:

1. A process for the recovery of monomeric values from the polymeric components of a first polymer-containing residue obtained in the preparation of styrene from alpha-methylbenzyl alcohol by dehydration of alpha-methylbenzyl alcohol to styrene which comprises distilling said residue in a first step to produce monomeric values from at least some of said residue and to remove at least some of said monomeric values as distillate and to leave a second polymer-containing residual material and thereafter distilling the second residual material remaining from the first stage in a second stage at a temperature higher than the temperature prevailing in the first stage and for a longer period of time to produce additional monomeric values from said polymer-containing residual material while removing said additional monomeric values as distillate, at least a part of said monomeric values being produced by the conversion of the polymeric components to monomeric values.

2. A process as defined in claim 1, wherein the process is carried out at a temperature of 180° to 275° C. in the first stage and a temperature of 300° to 425° C. in the second stage.

3. A process as defined in claim 1, wherein said first stage distillation is carried out in a batchwise manner at a pressure in the range of 5 to 100 mm Hg. and at a reboiler temperature of 180° to 260° C.

4. A process as defined in claim 3, wherein second stage distillation is carried out at a pressure of at least 500 mm Hg. and at a reboiler temperature of 325° to 375° C.

5. A process for the recovery of monomeric values from the polymeric components of a first polymer-containing residue obtained in the preparation of styrene from alpha-methylbenzyl alcohol by the dehydration of alpha-methylbenzyl alcohol to styrene which comprises distilling said residue in a first stage under subatmospheric pressure to produce monomeric values from at least some of said residue and to remove at least some of said product monomeric values as distillate and to leave as a bottom product a second polymer-containing residual material and thereafter distilling the second residual material remaining from the first stage in a second stage at a pressure and temperature higher than the temperature and pressure prevailing in the first stage to produce additional monomeric values from said polymer-containing residual material while removing said additional product monomeric values as distillate, at least a part of said monomeric values being produced by the conversion of the polymeric components to monomeric values.

6. A process as defined in claim 5, wherein the pressure in the second stage is at least 400 mm Hg.

7. A process as defined in claim 5, wherein said first stage distillation is carried out at a pressure in the range of 5 to 100 mm Hg and at a reboiler temperature of 180° to 260° C.

8. A process as defined in claim 7, wherein said second stage distillation is carried out at a pressure of at least 500 mm Hg and at a reboiler temperature of 300° to 425° C.

9. A process as defined in claim 5, wherein said first stage distillation is carried out at a reboiler temperature of 180° C. to 275° C.

10. A process as defined in claim 5, wherein said second stage distillation is carried out at a reboiler temperature of 300° C. to 425° C.

* * * * *